(12) United States Patent
Chapman

(10) Patent No.: US 12,213,822 B2
(45) Date of Patent: Feb. 4, 2025

(54) ELECTRONIC COLLIMATION AND DEPTH DETECTION IN A SIDE-VIEWING LAPAROSCOPIC PROBE FOR THE DETECTION OF HIGH ENERGY GAMMA RADIATION

(71) Applicant: Gregg J. Chapman, Plain City, OH (US)

(72) Inventor: Gregg J. Chapman, Plain City, OH (US)

(73) Assignee: Actis IP Holdings, LLC, Powell, OH (US)

( * ) Notice: Subject to any disclaimer, the term of this patent is extended or adjusted under 35 U.S.C. 154(b) by 134 days.

(21) Appl. No.: 17/148,716

(22) Filed: Jan. 14, 2021

(65) Prior Publication Data

US 2021/0219928 A1    Jul. 22, 2021

Related U.S. Application Data

(60) Provisional application No. 62/962,234, filed on Jan. 17, 2020.

(51) Int. Cl.
| | |
|---|---|
| A61B 6/42 | (2024.01) |
| A61B 1/313 | (2006.01) |
| A61B 6/40 | (2024.01) |
| G01T 1/161 | (2006.01) |
| G01T 7/00 | (2006.01) |

(52) U.S. Cl.
CPC ............ *A61B 6/425* (2013.01); *A61B 6/4258* (2013.01); *G01T 1/161* (2013.01); *G01T 7/00* (2013.01); *A61B 1/3132* (2013.01); *A61B 6/4057* (2013.01)

(58) Field of Classification Search
None
See application file for complete search history.

(56) References Cited

U.S. PATENT DOCUMENTS

| | | | | |
|---|---|---|---|---|
| 5,841,135 | A * | 11/1998 | Stoller | G01N 23/083 250/269.3 |
| 6,021,341 | A * | 2/2000 | Scibilia | G01T 1/161 600/407 |
| 2002/0168317 | A1* | 11/2002 | Daighighian | A61K 49/18 600/407 |
| 2005/0263711 | A1* | 12/2005 | Gerl | G01T 1/169 250/363.01 |

(Continued)

*Primary Examiner* — Katherine L Fernandez
*Assistant Examiner* — Farouk A Bruce
(74) *Attorney, Agent, or Firm* — Emerson, Thomson & Bennett, LLC; Roger D. Emerson; Peter R. Detorre

(57) ABSTRACT

The necessary detector configuration and mathematical algorithms to implement a lateral (side-viewing) field of view in a gamma detection probe designed for laparoscopic use is disclosed. For this application, the diameter of the probe is limited to 12 mm. A hybrid collimation design, using a combination of both electronic collimation and metallic shielding, allows the probe to detect gamma emissions form 15 KeV-1.0 MeV. In the lower energy range, the 1.52 mm tungsten shielding is sufficient to collimate the primary detector. Two additional detectors are used to provide electronic collimation and depth detection. The upper energy limit of 1.0 MeV is imposed to exclude the possibility of electron-positron pair production which occurs at energies of 1.022 MeV and greater.

6 Claims, 4 Drawing Sheets

(56) References Cited

U.S. PATENT DOCUMENTS

| | | | | |
|---|---|---|---|---|
| 2009/0177082 A1* | 7/2009 | Baerwolff | ............... | G01T 7/00 |
| | | | | 600/436 |
| 2010/0288936 A1* | 11/2010 | Call | ............... | G01T 1/161 |
| | | | | 250/370.13 |
| 2013/0261974 A1* | 10/2013 | Stewart | ............... | G01V 5/125 |
| | | | | 250/269.3 |
| 2017/0215823 A1* | 8/2017 | Ivanov | ............... | A61B 6/545 |

* cited by examiner

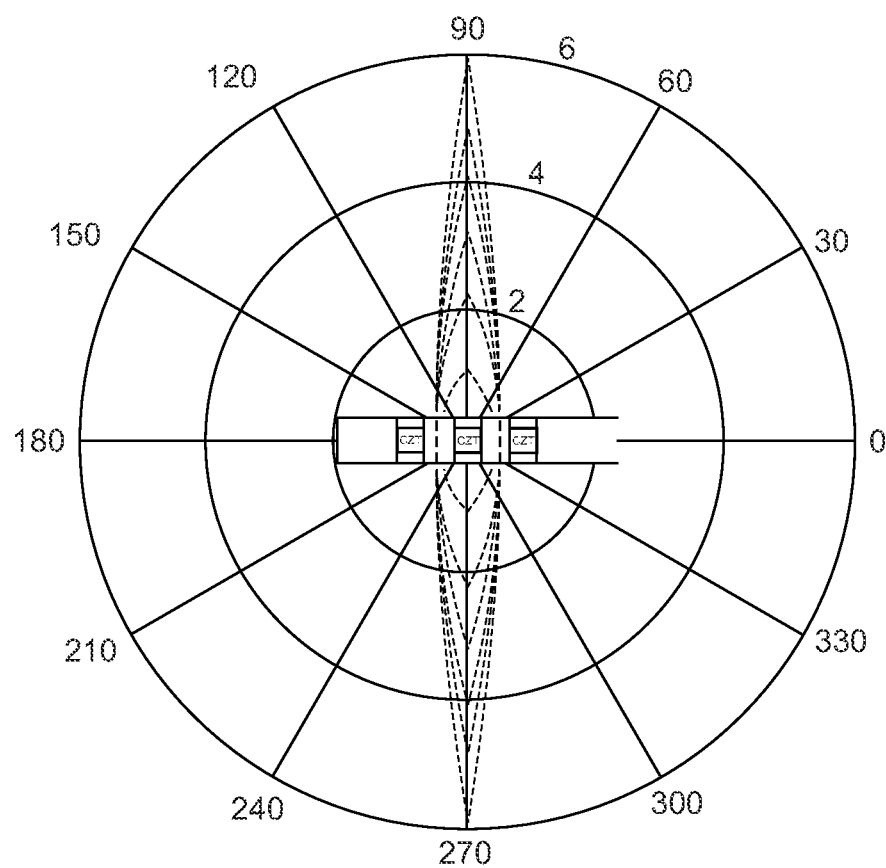
FIG. 4
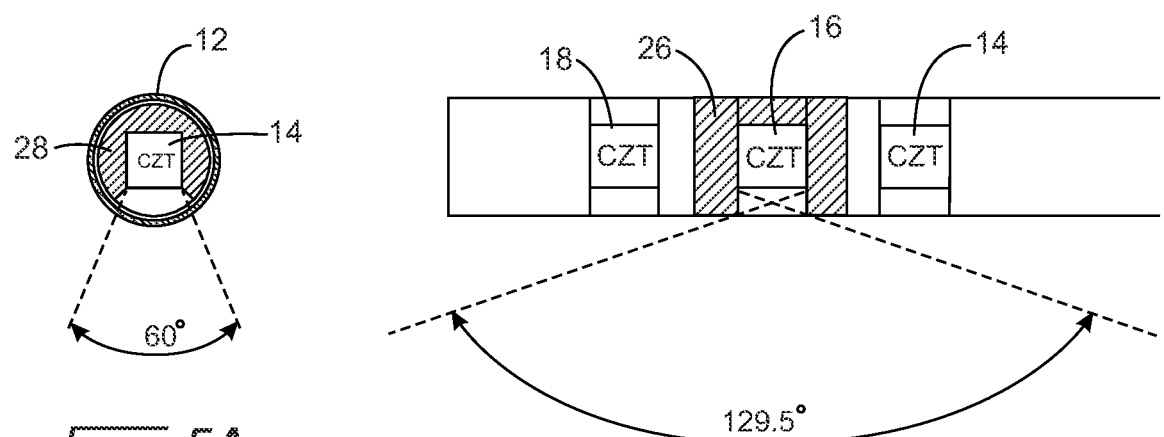
FIG. 5A
FIG. 5

ELECTRONIC COLLIMATION AND DEPTH DETECTION IN A SIDE-VIEWING LAPAROSCOPIC PROBE FOR THE DETECTION OF HIGH ENERGY GAMMA RADIATION

CROSS-REFERENCE TO RELATED APPLICATIONS

This application claims benefit of provisional 62/962,236 filed Jan. 17, 2020, and is cross-referenced to commonly owned U.S. Ser. No. 17/148,705, now U.S. Pat. No. 11,562, 454, provisional 62/962,232 filed January 17, entitled "A Compensated Dual Element Detector for Measuring the Distance to a Radio-Labeled Source", (provisional 62/962, 234 filed January 17, entitled "Electronic Collimation and Depth Detection in a Side-Viewing Laparoscopic Probe for the Detection of High Energy Gamma Radiation").

STATEMENT REGARDING FEDERALLY SPONSORED RESEARCH AND DEVELOPMENT

Not applicable.

THE NAMES OF THE PARTIES TO A JOINT RESEARCH AGREEMENT

Not applicable.

REFERENCE TO A "SEQUENCE LISTING," A TABLE, OR A COMPUTER PROGRAM

Not applicable.

STATEMENT REGARDING PRIOR DISCLOSURES BY THE INVENTOR OR A JOINT INVENTOR

Not applicable.

BACKGROUND OF THE INVENTION

Gamma-Guided Surgery has become the standard of care for localization of many pathological tissues in surgical oncology. Recent improvements in surgical technique have led to laparoscopic and robotic surgical approaches as opposed to open exposure of the surgical site, particularly in OB/GYN, urological, and abdominal procedures. Gamma detection probes that can be passed through a standard 12-millimeter port (Trocar™) are commercially available for the detection of radionuclides with low energy emissions (less than 300 KeV). In order to detect high energy gamma emission, such as the annihilation from residual positron emitting radioisotopes (511 KeV), heavy metal shielding of 9 mm thickness (radially) or greater is required. It is not possible to produce a probe capable of being passed through a 12-mm surgical port using this form of shielding. Chapman, G. J. (2017). "*High Energy Gamma Detection for Minimally Invasive Surgery*", (Doctoral dissertation), The Ohio State University, Columbus, OH, ProQuest Dissertations Publishing, 2019, 27539296 describes the use of multiple detector elements to limit the probe field of view without the use of heavy metal shielding. This electronic collimation compares the count rate of two or more detectors and applies a mathematical calculation based on the Inverse Squared Law to define the field of view. Probe counting is inhibited whenever the source is not within the calculated field of view. Electronic collimation differs from metallic shielding in that the field of view can be expanded or contracted by changing the numerical threshold for count activation within the control unit for the gamma probe. The depth of the active field of view also varies with the threshold value. For this reason, the depth of the radioactive source can be mathematically determined by the control unit. A preceding patent (USSN 62/862,984 filed on Jun. 18, 2019, now U.S. Ser. No. 16/904,126) adequately describes the detector configuration and signal processing to implement these features in an end-viewing probe.

BRIEF SUMMARY OF THE INVENTION

In this disclosure, the necessary detector configuration and mathematical algorithms to implement a lateral (side-viewing) field of view in a gamma detection probe designed for laparoscopic use is disclosed. For this application, the diameter of the probe is limited to 12 mm. A hybrid collimation design, using a combination of both electronic collimation and metallic shielding, allows the probe to detect gamma emissions from 15 KeV-1.0 MeV. In the lower energy range, the 1.52 mm tungsten shielding is sufficient to collimate the primary detector. Two additional detectors are used to provide electronic collimation and depth detection. The upper energy limit of 1.0 MeV is imposed to exclude the possibility of electron-positron pair production which occurs at energies of 1.022 MeV and greater.

BRIEF DESCRIPTION OF THE SEVERAL VIEWS OF THE DRAWINGS

For a fuller understanding of the nature and advantages of the present method and process, reference should be had to the following detailed description taken in connection with the accompanying drawings, in which:

FIG. 4 is an illustration of the extent of the electronically collimated field of view for count rate threshold settings ranging from 1.028 (6 cm depth) and 2.00 (1 cm depth).

FIG. 5 illustrates the field of view with the electronic collimation disabled.

FIG. 5A illustrates setting the lateral field of view at 60° by the tungsten shielding.

The drawings will be described in greater detail below.

DETAILED DESCRIPTION OF THE INVENTION

Figure 1:
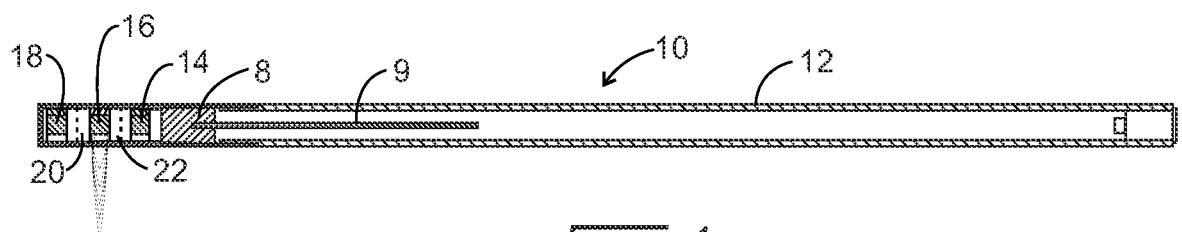
FIG. 1 illustrates the electronically collimated laparoscopic probe with a lateral field of view incorporates three gamma detectors in a probe of 12 mm diameter and a 475 mm (standard) length.
Figure 1A:
FIG. 1A is an end view of the laparoscopic probe illustrated in FIG. 1.
Figure 2:
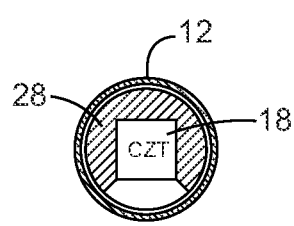
FIG. 2 illustrates tungsten shielding used to reduce the count rate of the middle detector outside of the 90° field of view. Two flanking detectors are surrounded by Teflon® instead of tungsten outside of the same 90° angle. The reduction in the count rate ratio disables counting when the source is not within the field of view subtended by the angle.
Figure 2A:
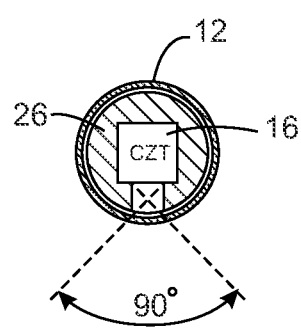
FIG. 2A illustrates the use of tungsten metal shielding for a central crystal and electronic collimation in combination to reduce the probe diameter to 12 mm or less.
Figure 2B:
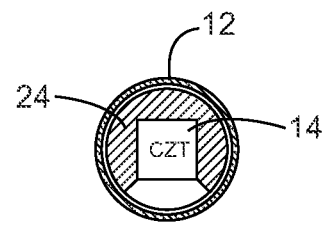
FIG. 2B illustrates that the outer crystals are held in place by insulated spacers.
Figure 3:
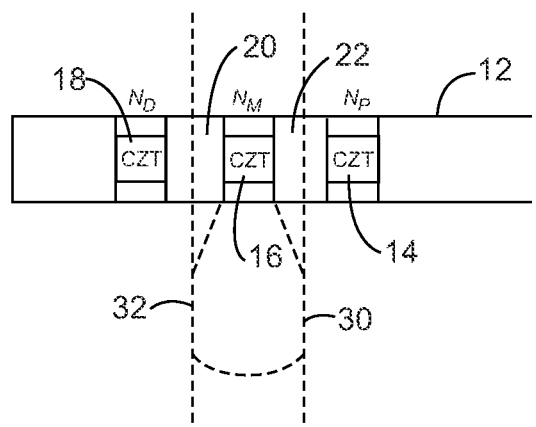
FIG. 3 illustrates the use of count rate ratios are used to limit the field of view to lay within two equidistant planes, as shown.

The side-viewing laparoscopic probe uses metallic and electronic collimation to limit the field of view to, say, a 90° angular arc about the longitudinal axis of the probe. The width, if the field of view perpendicular to the axis of the probe, is one centimeter. Electronic collimation limits the width and depth of the lateral field of view using three co-axial gamma detectors, either semiconductor or scintillation devices. The detector signals are pre-amplified by electronic circuitry in the head of the probe. The +12V medically isolated power is used to energize the pre-amplifiers. A 60-240V volt biasing voltage is applied to the anode of each of the crystal anodes. The cathodes are grounded. Power and signal lines may be supplied from the gamma detection system console, via a cable. Wireless modules and internal batteries could provide an alternative to the cable.
Probe Design The proposed implementation of a 12 mm diameter probe, 10, is illustrated in FIG. 1. The standard length of a laparoscopic probe in the medical industry is approximately 18 inches, or 475 mm. Also shown is a pre-amplifier bracket, 8, and pre-amplifier(s), 9. All probe materials are enclosed within medical grade 316 stainless steel or aluminum annular housing, 12. The lateral field of view can be divided into three regions (FIG. 3, between and on each side of the two dotted lines), each containing a gamma detection crystal, 14, 16, and 18. The 5 mm×5 mm×5 mm crystals are separated by a fixed distance of 1 centimeter using insulated spacers, 20 and 22, such as Teflon®. All three cathodes are oriented facing the same direction, as are the anodes. A 60-240V bias voltage is applied to the anodes of each detector, and all three cathodes are connected to an isolated ground. The extent of the field of view along the axis of the probe is limited to a volume between two imaginary planes that lay halfway between the central detector and the two flanking detectors. The field of view extends in all directions inside the surface of the planes.
Electronic Collimation The laparoscopic probe design uses tungsten metal shielding, 26, for central crystal 16, as seen in FIG. 2A and electronic collimation in combination to reduce the probe diameter to 12 mm or less. Outer crystals 14 and 18 are held in place by insulated spacers, 24 and 28, for crystals 14 and 18, respectively, as seen in FIG. 2B. The extent of the field of view along the axis of the probe is limited to a volume between two imaginary planes, 30 and 32, (see FIG. 3) that lay halfway between the middle detector and the two flanking detectors. A count rate ratio of middle detector 16 is divided by the count rate of either of the flanking detectors 14 and 18 from a gamma source located on the surface of either plane would result in a value of one. If the gamma source is distal to plane 32 between front detector 18 and middle detector 16, the count rate ratio of distal detector 14 divided by the count rate of middle detector 16 will be less than 1 and counting is inhibited by the gamma detection system control unit. If the gamma source is proximal to plane 30 half-way between middle 16 and proximal detector 14, the count rate ratio of proximal detector count rate divided by the middle detector count rate will be less than 1 and the control unit also inhibits counting.

While evaluation of these two ratios limits the field of view to a disk-shaped volume centered around the middle detector, additional collimation is required to limit the active field of view to a wedge-shaped area of, for example 90° (FIG. 2B) within the disked shaped region. To impose the angular limitation, a hybrid technique of collimation is used. Hybrid collimation, in general, is defined in patent, provisional 62/962,235 filed Jan. 17, 2020, entitled "Hybrid Collimation to Limit Field of View for Gamma Detection Probes at High and Low Energies".

For the present application, middle detector 16 is surrounded with tungsten cylinder 26, 1.5 mm thick, and with a 90-degree aperture, aligned with the cathode of the middle detector. Whenever the gamma source is within the 90° arc of the open aperture, no gamma radiation is blocked. Outside of the 90° arc, the tungsten shielding is sufficient to attenuate the gamma count by 32% at 511 KeV. Flanking crystals 14 and 18 contain no tungsten shielding, but Teflon® insulation 24 and 28 outside of the 90° arc. Since the count rate of the middle detector is attenuated outside of the angular field of view, the count rate ratios of the following equation are similarly reduced by 32%, forcing the count rate ratios to a value less than unity. Outside of the 90° arc, the count rate ratios are less than 1, and counting is inhibited by the probe control unit.

$$\frac{N_M}{N_D} \text{ or } \frac{N_M}{N_P} = 0.68 \frac{N_M}{N_{either}} \text{ outside the } FOV$$

$N_M$ is the counts received on the middle detector $N_D$ is the counts received on the distal (front flanking) detector $N_P$ is the counts received on the proximal (rear flanking) detector U.S. Ser. No. 16/904,126 and Chapman, G. J. (2017). "High Energy Gamma Detection for Minimally Invasive Surgery", (Doctoral dissertation), The Ohio State University, Columbus, OH, ProQuest Dissertations Publishing, 2019, 27539296 disclose that the distance to the radiation source also can be calculated from the count rate ratio of two detectors. The methodology described in this disclosure is to be incorporated in the embodiment of an electronically collimated probe consisting of two or more detectors and is an integral part of the probe design. In this disclosure, the mathematics and a calculation that define a variable field of view for a side-viewing gamma probe consisting of three semiconductor, or other material, gamma detectors, separated by a known fixed distance, is disclosed.
Compensation Unlike the end viewing field of view, the lateral field of view does not contain overlap in the apparent aspect of any of the three detectors; for this reason, no count correction for the shielding effect of other detectors is necessary in this geometry. Since tungsten shielding 26 around middle detector 16 is intended to attenuate count rates, either for shielding at low energies, or attenuation of the count rate ratio at high energies, no compensation factor is required for shielding effects in this design.

All three detector count rates are corrected for background radiation. The background count rate measurement is acquired by placing the field of view over an area of the surgical bed that is known to contain no radiolabeled pathological tissue, but is presumed to contain the same blood pool background radiation as the surgical bed to be surveyed for focal concentrations of the radiolabeled agent. The averaged background count rate acquired at each detector, taken over a, say, three-second period, is subtracted from the averaged count rate for all subsequent measurements. For this reason, crystals chosen for the laparoscopic probe must be carefully chosen and calibrated to match the sensitivity of all three detectors.

Note that the tungsten shielding serves two purposes in the probe design. It reduces the count rate of the middle detector outside of the angular field of view of 90°. The tungsten also is of sufficient thickness to collimate the middle crystal by attenuating the incident radiation from energies lower than 234 KeV. At 234 KeV the count rate of the middle detector is reduced by 80%. It is reduced more at lower energies.

Depth Detection and Field of View

Since the probe is electronically collimated, the distance to the radiation source can be estimated using one of two mathematical calculations. The first calculation estimates the distance based on the comparison of the count rates from each of the three crystals, and application of the Inverse Squared Law.

$$N = \propto \frac{S}{d^2}$$

Since the number of counts received at the detector is proportional to the inverse of the distance to the source, squared, N is the number of counts received
S is the counts emitted from the source
d is the distance to the source counts received at the three detectors separated by a known, fixed distance is sufficient data to calculate the distance to the radiation source.

$$d = \frac{x}{\left(\sqrt{\frac{N_M}{N_F}} - 1\right)}$$

Figure 8:
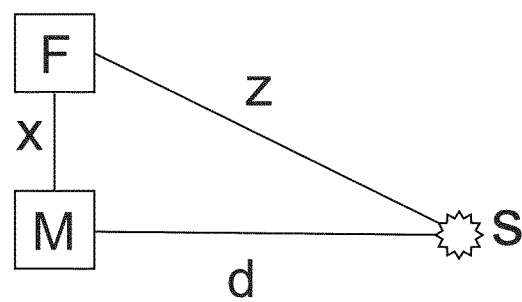
FIG. 8 is a diagram showing the positioning of a flanking detector and a middle detector with respect to one another and with respect to the radiation source.

In reference to the diagram shown in FIG. 8:
F is the flanking detector
M is the middle detector
X is the known separation between detectors'
d is the distance to the source
S indicates the radiation source The second method, incorporated in the control unit, takes advantage of the fact that electronic collimation limits the extend the field of view (FIG. 4). The software algorithm begins by setting the field of view to extending, for example, 6 cm into the tissue. As the field of view is reduced in depth by changing the counting threshold, the counts from the primary radiation source will abruptly drop out of the counting range of the detectors. At this setting, the radiation source is calculated to be just beyond the extent of the field of view. A slight increase in the field of view is sufficient to verify that the counts are again received at the detectors.

Notice in FIG. 4 that the width, if the field of view changes very little, as the counting threshold increases to extend the depth of the field of view. Moreover, the angular extent if the lateral field of view is fixed at 60° by the aperture of the tungsten shielding (FIG. 5A). Thus, the width of the field is a function of the distance between the detectors, and the angle is a function of the tungsten geometry. The depth is the only parameter that can be varied under software control in the side-viewing configuration.

This suggests that it may be of benefit to disable electronic collimation until a target of interest is localized using only the middle detector and proximity to the radiation source. The tungsten shielding would provide 32% attenuation outside of the 90° angular aperture. The field of view would have an angular field of view of 129.5° in the longitudinal direction imposed by the geometry of the tungsten shield. (FIG. 5).

Control Unit Connection

Figure 6:
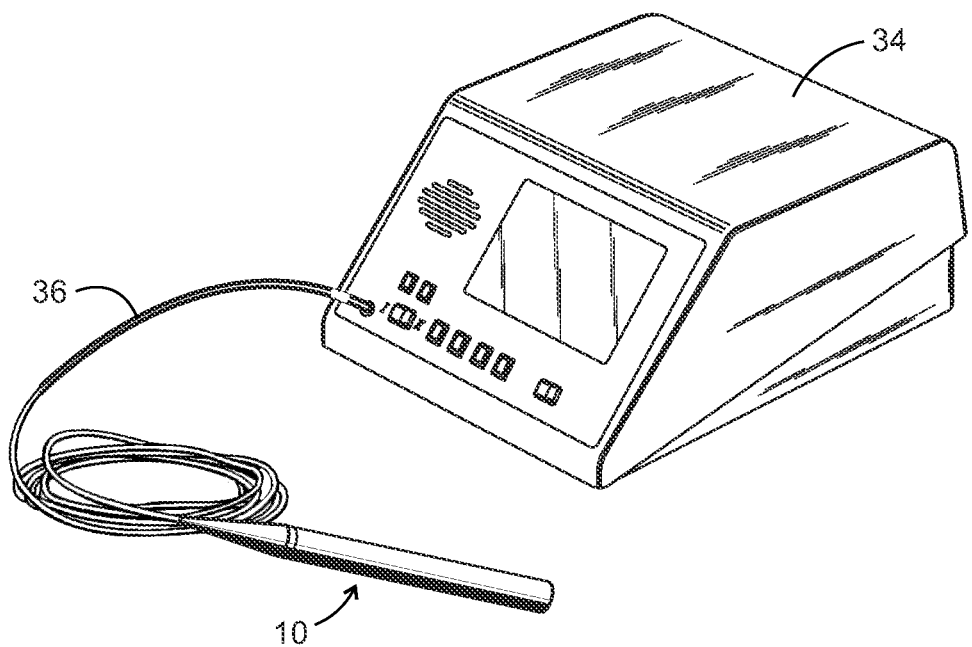
FIG. 6 illustrates a gamma detection control unit and hand-held probe.

In FIG. 6, laparoscopic probe 10 is attached to a console, 34, via a cable, 36, such as is described in representative U.S. Pat. Nos. 4,801,803, 4,889,991, 5,441,050, 6,144,876, and others. Except as is described below, the operation of such probes and console pairs of the disclosed probe/console is like that described in the cited patents, which are expressly incorporated herein by reference.

Figure 7:
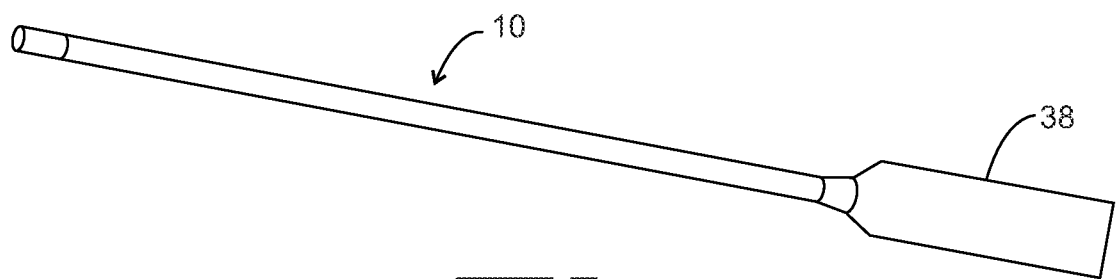
FIG. 7 illustrates a probe having a handle and a wireless transceiver module.

The pre-amplifier electronics for each of the three detector signals is enclosed within the stainless-steel tubing 12 of the probe housing. If the probe is connected to control unit 34 using multi-conductor cable 36, the number of conductors required may make the cable large and inconvenient to use in a surgical setting. The minimum number of conductors is seven: power, ground, bias voltage, detector 1, detector 2, detector 3, and shield. If the necessary power supply can be housed in an extension to the probe handle, 38, as in FIG. 7, a wireless transceiver module could be incorporated as well, obviating the need for a cable. Commercially available Bluetooth™ transceivers have been incorporated in wireless gamma detection probes in the past. Other wireless standards could also be considered.

While the apparatus, system, and method have been described with reference to various embodiments, those skilled in the art will understand that various changes may be made and equivalents may be substituted for elements thereof without departing from the scope and essence of the disclosure. In addition, many modifications may be made to adapt a particular situation or material in accordance with the teachings of the disclosure without departing from the essential scope thereof. Therefore, it is intended that the disclosure should not be limited to the particular embodiments disclosed, but that the disclosure will include all embodiments falling within the scope of the appended claims. In this application all units are in the metric system and all amounts and percentages are by weight, unless otherwise expressly indicated. Also, all citations referred herein are expressly incorporated herein by reference.

The invention claimed is:

1. A side-viewing laparoscopic probe (10) for detecting a source of radiation emissions from 15 KeV-1.0 MeV, which comprises:
   (a) an elongate annular housing (12) having a forward end and a rear end, and having a longitudinal axis;
   (b) a middle radiation detecting element (16) located within the elongate annular housing, the middle radiation detecting element (16) having a middle radiation detecting element field of view and surrounded by a radiation blocking shielding (26) arranged to reveal a defined side field of view and a pair of flanking co-axial radiation detecting elements (14, 18), including a proximal radiation detecting element and a distal radiation detecting element, each of said pair of flanking co-axial radiation detecting elements having a field of view and devoid of radiation blocking shielding, the pair of flanking co-axial radiation detecting elements located at the forward end of and within the elongate annular housing and oriented for a lateral field of view, wherein co-axial insulated spacers (20, 22) are located on either side of the middle radiation detecting element and adjacent to and in between each of the pair of flanking co-axial radiation detecting elements, the middle radiation detecting element, the pair of flanking co-axial radiation detecting elements, and the insulated spacers being co-axial along the elongate annular housing longitudinal axis; and (c) one or more pre-amplifiers (9) located adjacent and rearward of the flanking co-axial radiation detecting elements and in electrical connection therewith and configured to be in communication with a console housing a software algorithm that disables radiation counting when a source of radiation is outside the defined side field of view, wherein a count rate of the middle radiation detecting element is attenuated outside of the middle radiation detecting element field of view, such that the count rate ratio of $N_m/N_p$ or $N_m/N_d$ is reduced by 32% outside the field of view of the middle radiation detecting element, forcing the count rate ratios to a value less than unity, where $N_M$ is the counts received on the middle radiation detecting element, $N_D$ is the counts received on the distal radiation detecting element, and $N_P$ is the counts received on the proximal radiation detecting element.

2. The side-viewing laparoscopic probe of claim 1, wherein the probe is in wireless communication with the console.

3. The side-viewing laparoscopic probe of claim 1, wherein counts from the proximal, middle and distal radiation detecting elements are corrected for background radiation.

4. The side-viewing laparoscopic probe of claim 1, wherein the defined side field of view for the middle radiation detecting element is 90°.

5. The side-viewing laparoscopic probe of claim 1, wherein radiation blocking shielding is tungsten.

6. The side-viewing laparoscopic probe of claim 1, wherein the probe is effective for detecting a source of radiation emissions of less than 300 KeV.

\* \* \* \* \*